US010945427B2

(12) United States Patent
Nishimura et al.

(10) Patent No.: US 10,945,427 B2
(45) Date of Patent: Mar. 16, 2021

(54) TREHALOSE AND DEXTRAN-CONTAINING SOLUTION FOR TRANSPLANTING MAMMALIAN CELLS

(71) Applicant: OTSUKA PHARMACEUTICAL FACTORY, INC., Tokushima (JP)

(72) Inventors: Masuhiro Nishimura, Tokushima (JP); Tamaki Wada, Tokushima (JP); Chikage Shirakawa, Tokushima (JP); Masako Doi, Tokushima (JP)

(73) Assignee: OTSUKA PHARMACEUTICAL FACTORY, INC., Tokushima (JP)

( * ) Notice: Subject to any disclaimer, the term of this patent is extended or adjusted under 35 U.S.C. 154(b) by 162 days.

(21) Appl. No.: 14/895,366

(22) PCT Filed: Jun. 18, 2014

(86) PCT No.: PCT/JP2014/003266
§ 371 (c)(1),
(2) Date: Dec. 2, 2015

(87) PCT Pub. No.: WO2014/208053
PCT Pub. Date: Dec. 31, 2014

(65) Prior Publication Data
US 2016/0120170 A1    May 5, 2016

(30) Foreign Application Priority Data
Jun. 28, 2013 (JP) .............................. JP2013-137454

(51) Int. Cl.
*A01N 1/02* (2006.01)
*A61K 9/00* (2006.01)
*A61K 35/28* (2015.01)

(52) U.S. Cl.
CPC .............. *A01N 1/0226* (2013.01); *A01N 1/02* (2013.01); *A01N 1/021* (2013.01); *A01N 1/0221* (2013.01); *A61K 9/008* (2013.01); *A61K 35/28* (2013.01)

(58) Field of Classification Search
CPC ........ A01N 1/0226; A01N 1/02; A01N 1/021; A01N 1/0221; A61K 9/08; A61K 35/28
See application file for complete search history.

(56) References Cited

U.S. PATENT DOCUMENTS

2009/0081785 A1    3/2009  Ho et al.
2009/0239206 A1    9/2009  Koshiba et al.
(Continued)

FOREIGN PATENT DOCUMENTS

EP        0580444 A1    1/1994
EP        1516923 A2    3/2005
(Continued)

OTHER PUBLICATIONS

Fred H. Gage, "Mammalian Neural Stem Cells", Stem Cell Research and Ethics, Feb. 25, 2000, pp. 1433-1438, Science, vol. 287.
(Continued)

*Primary Examiner* — Louise W Humphrey
*Assistant Examiner* — Charles Zoltan Constantine
(74) *Attorney, Agent, or Firm* — Greenblum & Bernstein, P.L.C.

(57) ABSTRACT

The problem of the present invention is to provide a method for preserving mammalian cells over a long period of time using a solution for cell transplantation, capable of effectively suppressing cell death when the mammalian cells have been preserved, and the solution for cell transplantation. The present invention is characterized in that mammalian cells are preserved in a physiological aqueous solution for cell transplantation, comprising 2.0 to 6.0% (w/v) of
(Continued)

| Solutions in Figure 1 and Figure 2 | | Trehalose Concentration | Dextran Concentration |
|---|---|---|---|
| Comparative Example | a | 3% | 0% |
| | b | 3% | 1% |
| | c | 3% | 3% |
| Present Invention | A | 3% | 5% |
| | B | 3% | 7% | trehalose, a derivative thereof, or a salt of trehalose or the derivative (a trehalose) and 4.0 to 7.0% (w/v) of dextran, a derivative thereof, or a salt of dextran or the derivative (a dextran). The effects of a trehalose and a dextran contained in the physiological aqueous solution for cell transplantation can suppress a decrease in the cell survival rate when mammalian cells are preserved for a long period of time (at least 14 days).

10 Claims, 8 Drawing Sheets

(56) References Cited

U.S. PATENT DOCUMENTS

| | | | |
|---|---|---|---|
| 2010/0028883 A1* | 2/2010 | Kobayashi | C12Q 1/66 435/6.13 |
| 2010/0047213 A1 | 2/2010 | Zeitlin et al. | |
| 2013/0260461 A1 | 10/2013 | Kobayashi et al. | |

FOREIGN PATENT DOCUMENTS

| | | |
|---|---|---|
| JP | 3253131 B2 | 2/2002 |
| JP | 2012-115253 A | 6/2012 |
| WO | 2007/043698 A1 | 4/2007 |
| WO | 2010/021714 A2 | 2/2010 |
| WO | 2012/063870 A1 | 5/2012 |
| WO | 2012/133575 A1 | 10/2012 |

OTHER PUBLICATIONS

Sean J. Morrison et al., "Prospective Identification, Isolation by Flow Cytometry, and In Vivo Self-Renewal of Multipotent Mammalian Neural Crest Stem Cells", Cell Press, Mar. 5, 1999, pp. 737-749, Cell, vol. 96.

Eduard Battle et al., "B-Catenin and TCF Mediate Cell Positioning in the Intestinal Epithelium by Controlling the Expression of EphB/EphrinB", Cell Press, Oct. 18, 2002, pp. 251-263, Cell, vol. 111.

Thomas A. Lane et al., "Liquid storage of marrow stromal cells", Transplantation and Cellular Engineering, Jul. 2009, pp. 1471-1481, vol. 49.

Fengshi Chen et al., "Development of New Organ Preservation Solutions in Kyoto University", Department of Thoracic Surgery, Graduate School of Medicine, 2004, pp. 1107-1114, vol. 45, No. 6.

International Search Report issued with respect to application No. PCT/JP2014/003266, dated Sep. 22, 2014.

International Preliminary Report on Patentability issued with respect to application No. PCT/JP2014/003266, dated Dec. 29, 2015.

European Search Report issued with respect to application No. 14818277.7, dated Oct. 18, 2016.

Katsunori Aoki et al., "A comparison of Ringer's lactate and acetate solutions and resuscitative effects on splanchnic dysoxia in patients with extensive burns," 36 BURNS 1080-1085 (2010).

* cited by examiner

Reference Material 1: Figure 1 of the present application and supplemental explanations
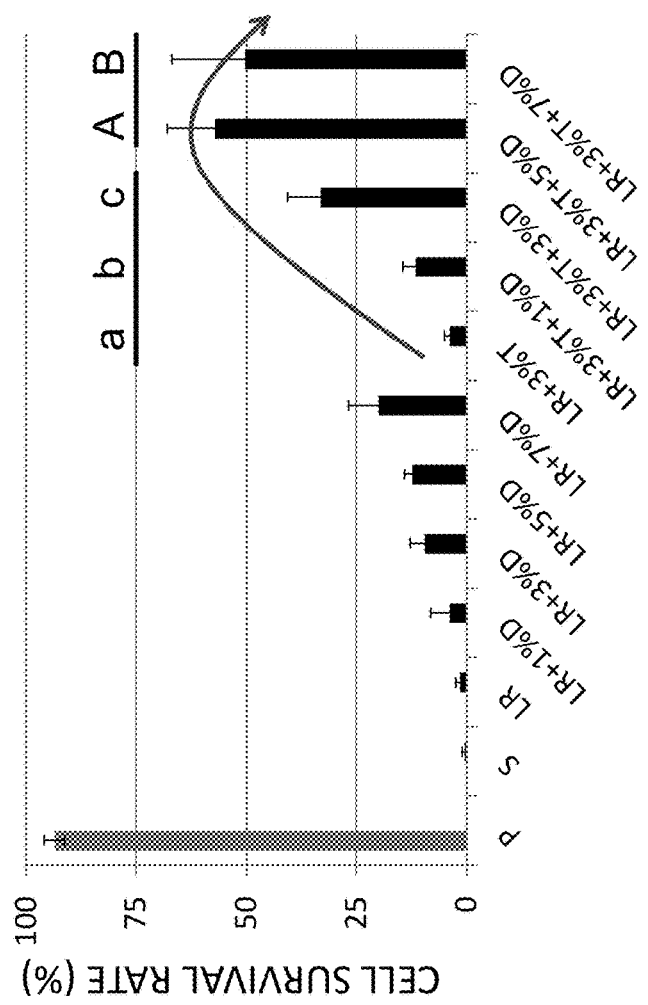

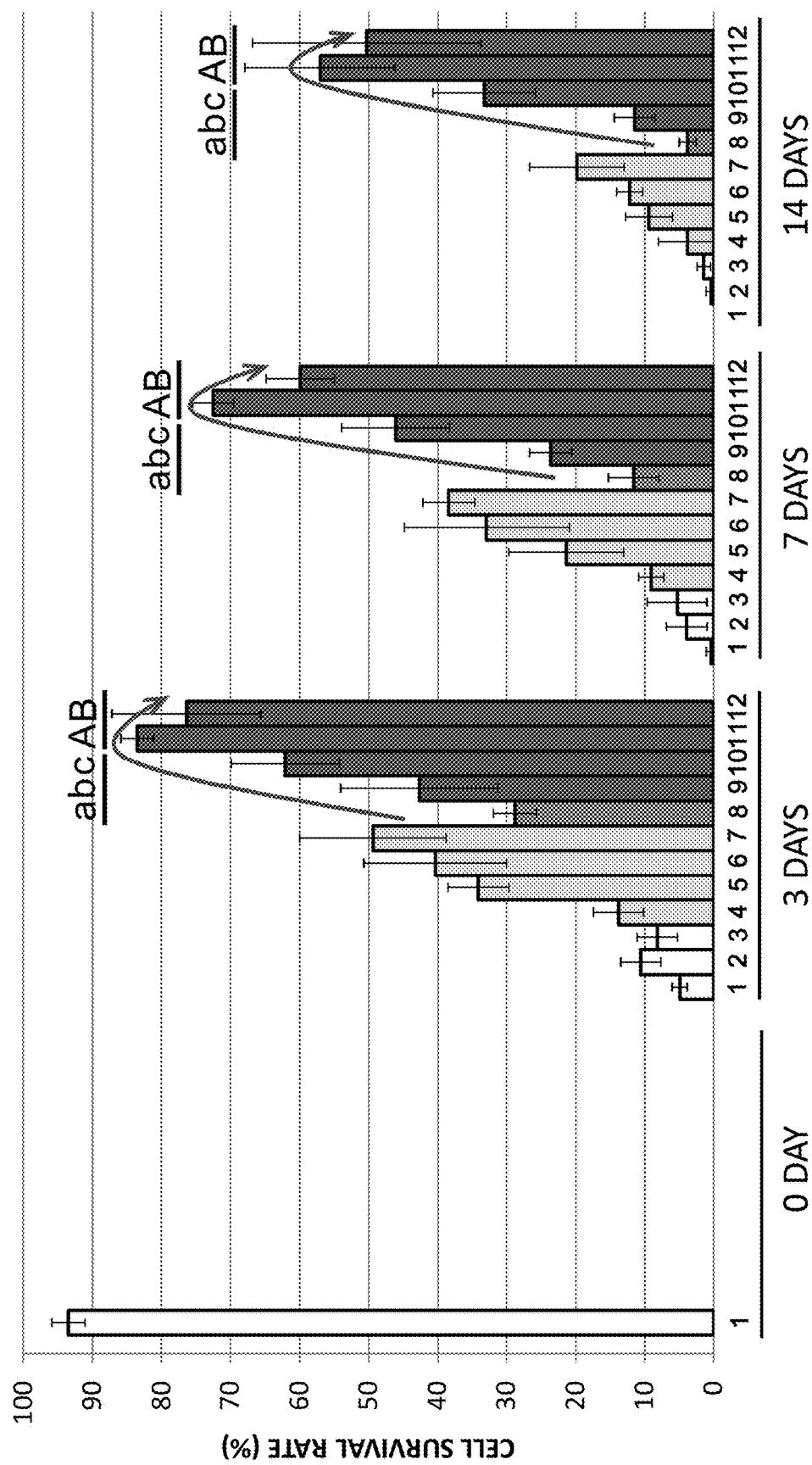

Reference Material 3 : Figure 3 of the present application and supplemental explanations
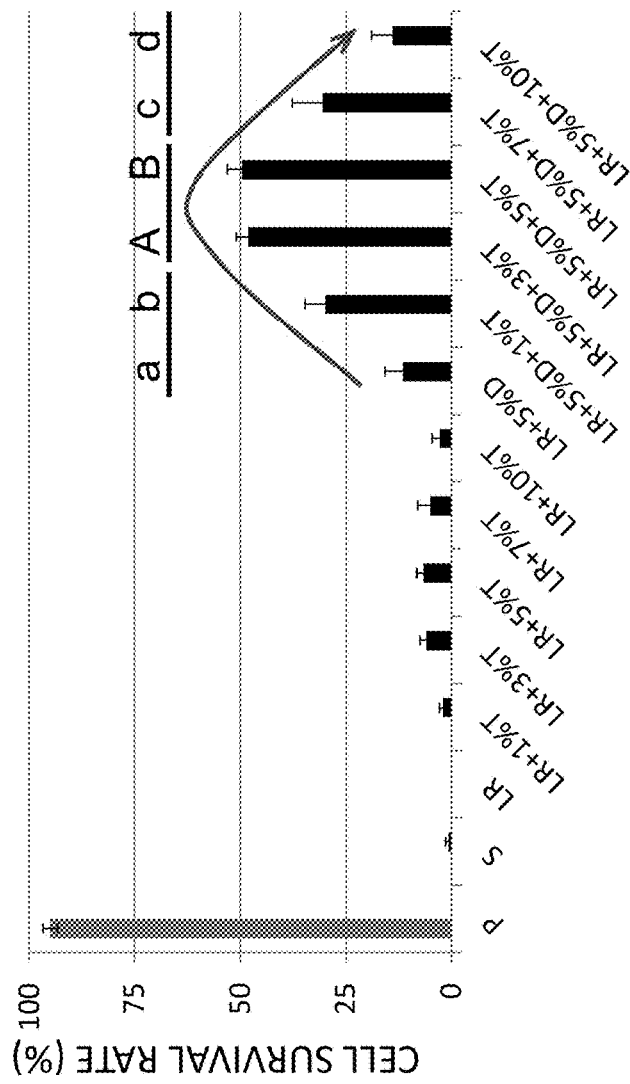

Reference Material 4: Figure 4 of the present application and supplemental explanations
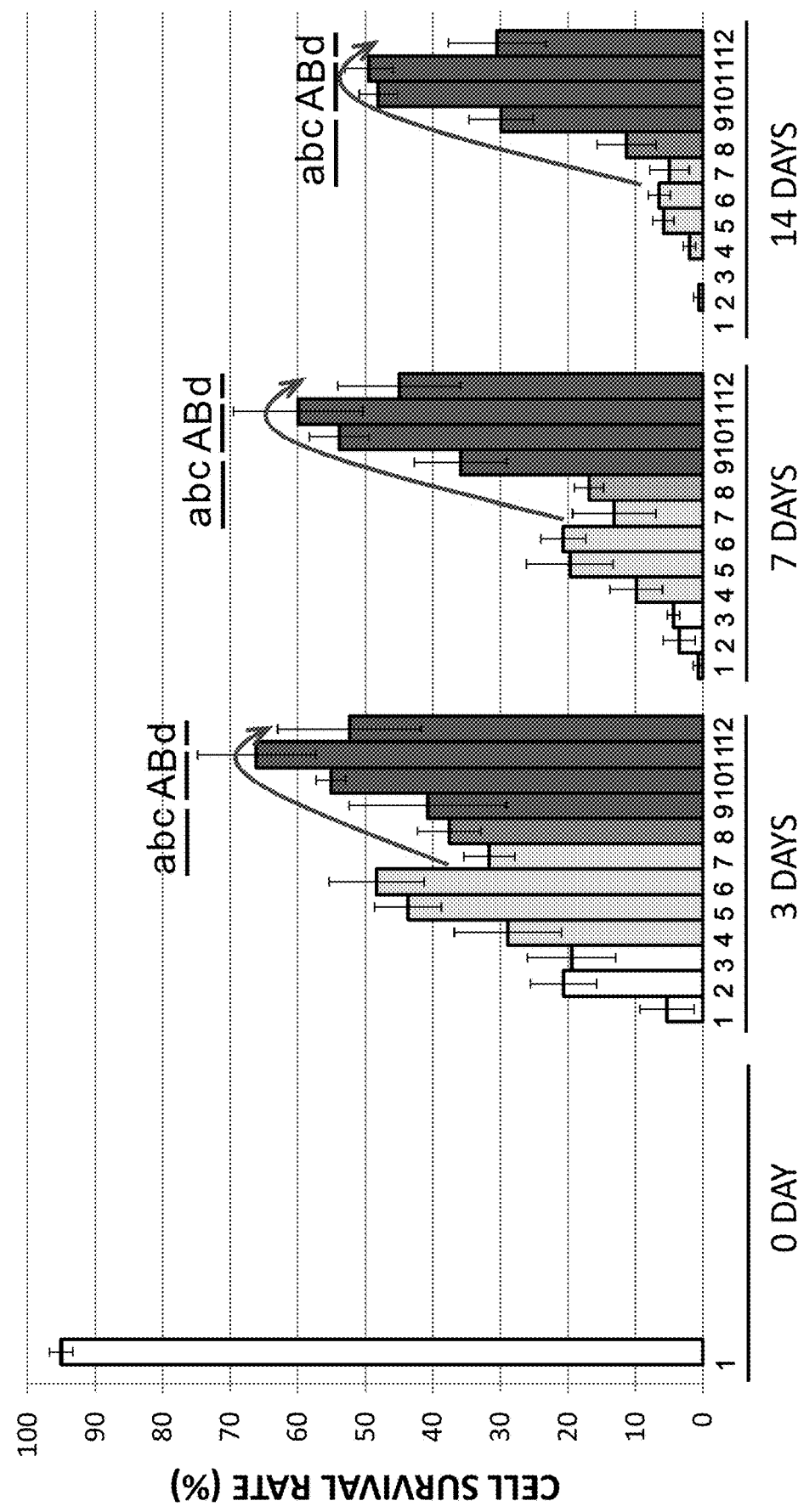

[Figure 5]
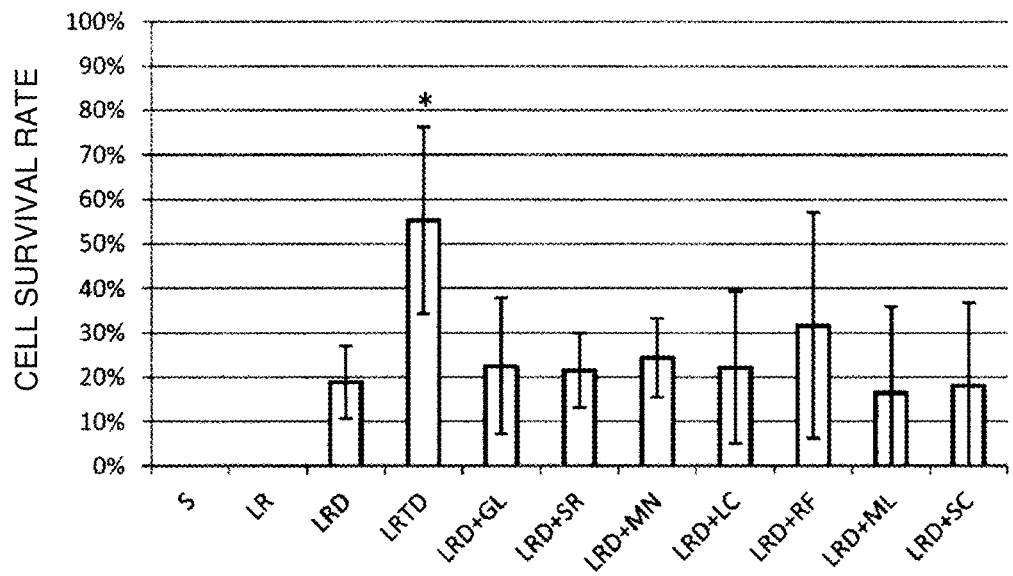
[Figure 6]
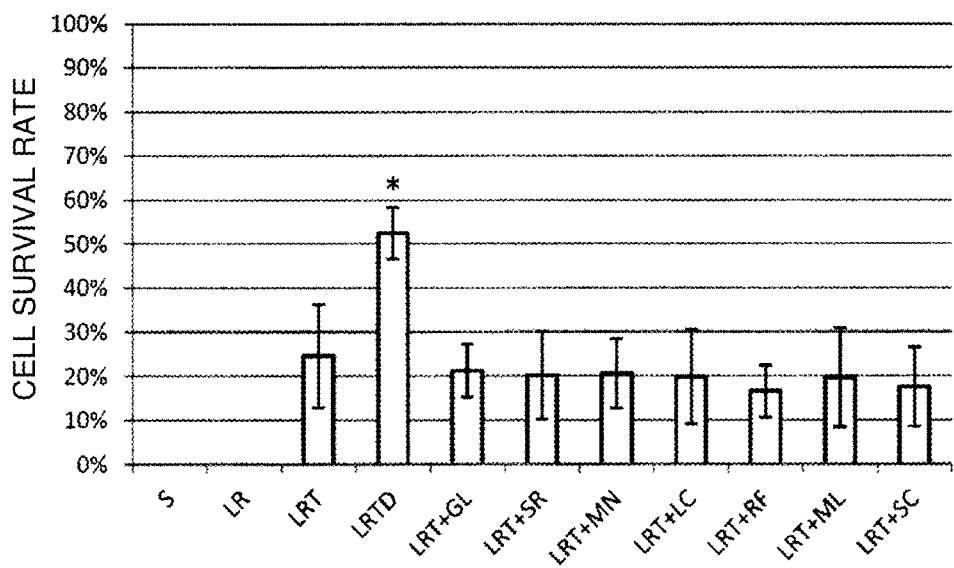
Dunnett's test vs LRT, *: p< 0.05, N=4

[Figure 7]
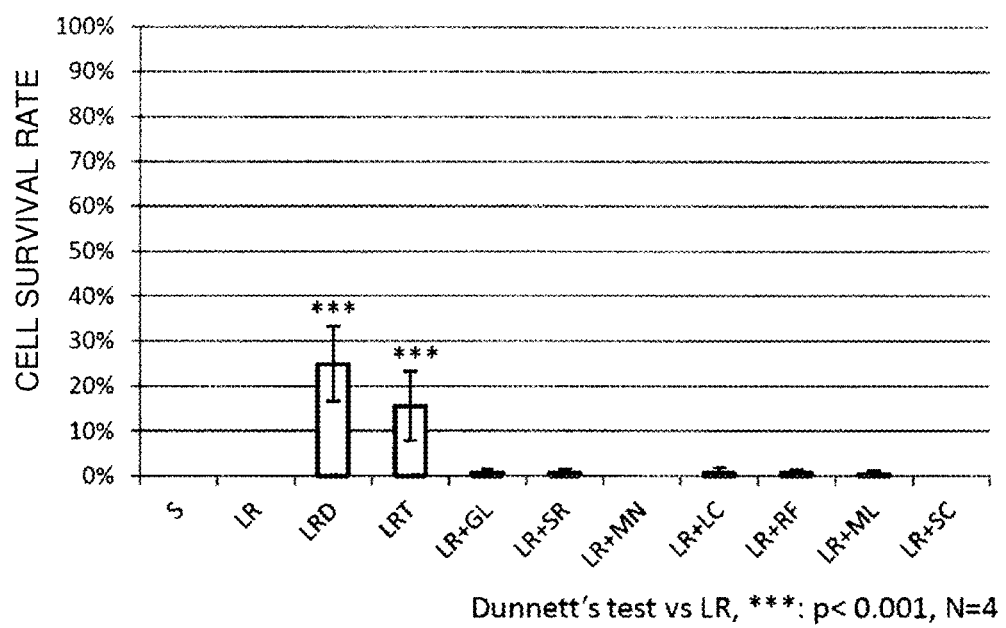

[Figure 8]
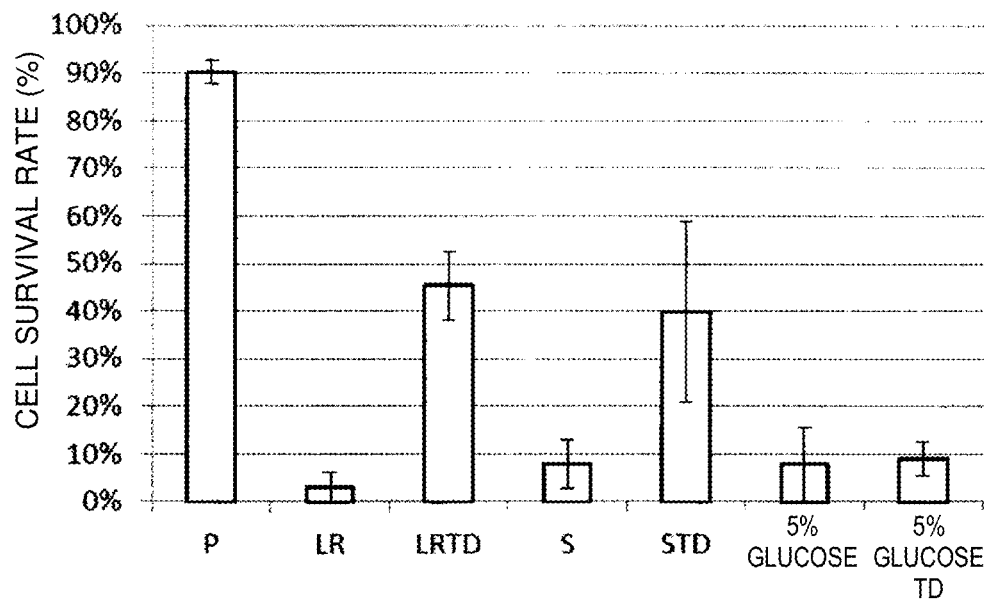
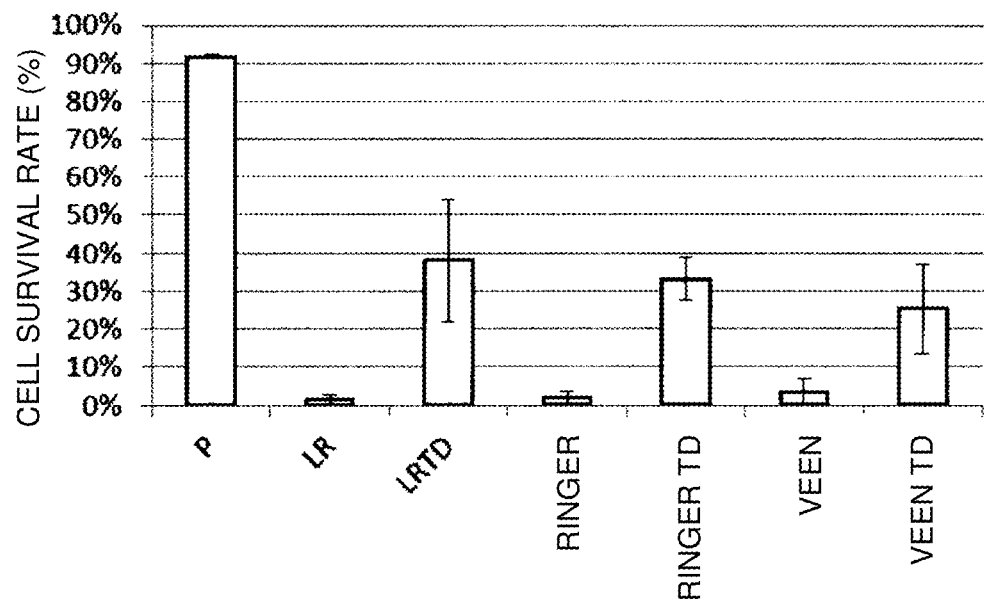

[Figure 9]
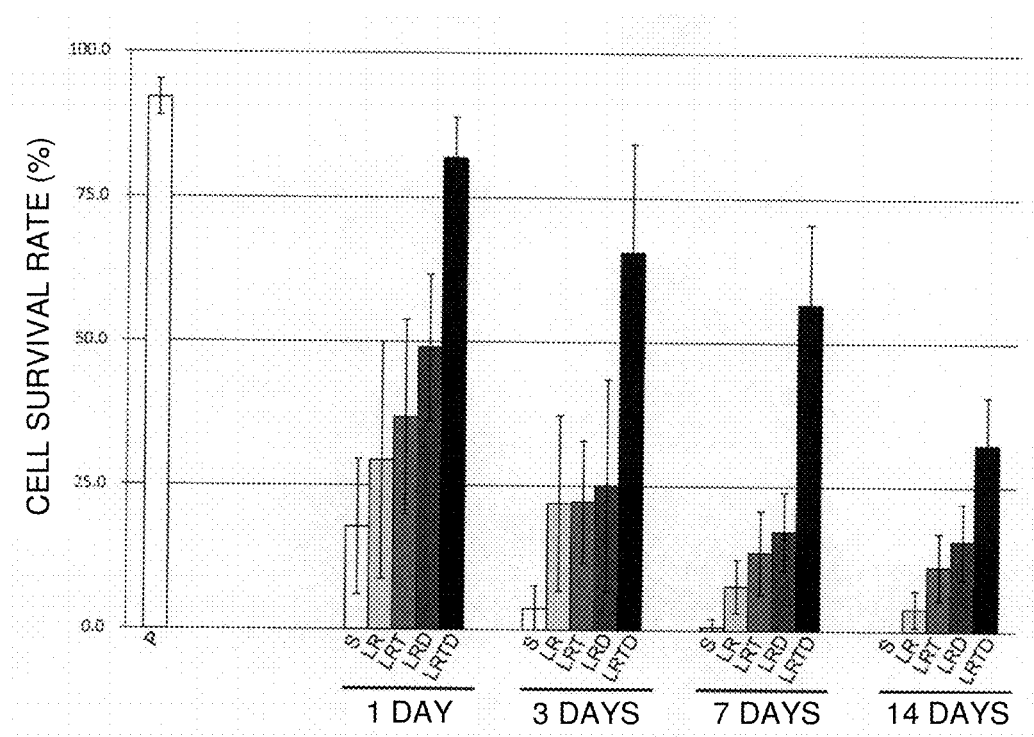

TREHALOSE AND DEXTRAN-CONTAINING SOLUTION FOR TRANSPLANTING MAMMALIAN CELLS

TECHNICAL FIELD

The present invention relates to a method for preserving mammalian cells in a physiological aqueous solution for cell transplantation comprising 2.0 to 6.0% (w/v) of trehalose, a derivative thereof, or a salt of trehalose or the derivative (hereinafter, sometimes referred to as "a trehalose") and 4.0 to 7.0% (w/v) of dextran, a derivative thereof, or a salt of dextran or the derivative (hereinafter, sometimes referred to as "a dextran") (hereinafter, sometimes referred to as "the present solution for cell transplantation"), the present solution for transplantation, and a physiological aqueous solution containing cells for transplantation comprising mammalian cells and a trehalose and a dextran (hereinafter, referred to as "the present solution containing cells for transplantation").

BACKGROUND ART

In recent years, rapid progress of stem cell studies has increased momentum toward regenerative medicine, and the knowledge and understanding thereof has been widespread not only in researchers but also in the public. Regenerative medicine using stem cells is medicine intended for reestablishing the function of cells and tissues damaged by various diseases by utilizing the self-renewal potential and pluripotency of the stem cells or factors secreted by the stem cells. Bone-marrow transplantation in patients having intractable hematological diseases, such as leukemia and aplastic anemia, results in the engraftment of hematopoietic progenitors in the body of these patients, which enables the maintenance of hematopoietic capacity over almost entire life. Recently, many researchers have aimed at clinical application using stem cells other than hematopoietic stem cells, have identified stem cells in central nerves, peripheral nerves, bone marrow, small intestine, and the like, and have begun to implement the tissue stem cell transplantation treatment of traumatic disease and tissue degeneration disease (Non-patent Documents 1 to 3). On the other hand, cancer immune cell therapy is the most advanced cell medicine in which immune cells acting to attack cancer are taken to the outside of the body, followed by enhancing the action and then again returning the cells to the inside of the body, and therapies using T cells are implemented, such as dendritic cell vaccine therapy, alpha/beta T cell therapy ($\alpha\beta$ T cell therapy), gamma/delta T cell therapy ($\gamma\delta$T cell therapy), CTL therapy, and natural killer cell therapy (NK cell therapy).

When stem cells or T cells used for transplantation treatment is preserved for a long period of time, preservation in a liquid cannot keep the survival rate of the cells satisfactory. For example, the chilled preservation (at 4° C.) of human bone marrow stem cells in saline is reported to decrease the cell survival rate to 40% or less after 48 hours and to 20% or less after 72 hours (Non-patent Document 4). Thus, when stem cells for transplantation or T cells for transplantation are preserved for a long period of time, freeze preservation is commonly carried out. However, freeze preservation liquid typically contains a freeze preservation agent, such as DMSO or glycerol; thus, it is necessary to remove the freeze preservation agent for transplantation before performing transplantation treatment after thawing freeze-preserved stem cells or T cells, which has been considered problematic because of being labor-intensive. The freeze preservation liquid containing a freeze preservation agent has also been considered problematic in that it results in the significant damage of the cytoskeleton due to the crystallization of water during freezing and decreases the cell survival rate after freezing and thawing. Thus, there has been considered to be an urgent need for the development of a cell preservation liquid excellent in the simplicity of use and capable of suppressing a decrease in the cell survival rate.

Trehalose is a type of disaccharide formed by the 1,1-glycoside linkage of glucoses. Trehalose is used in various foods and cosmetics because it presents a sweet taste and has a high water-retaining capacity. Trehalose is also used as an active ingredient of an organ-protecting solution in transplanting the organ because it has the properties of stabilizing cell membrane and suppressing cell damage. For example, excellent organ preservation solutions containing trehalose have been developed, such as ET-Kyoto solution and New ET-Kyoto solution (Patent Documents 1 and 2 and Non-patent Document 5).

Dextran is a type of polysaccharide consisting of glucose and is widely used as a thickener, a humectant, or the like in the fields of medicine and cosmetics.

The present inventors have reported that the washing of mesenchymal stem cells detached from a cell culture vessel by proteolytic enzyme treatment with a trehalose-containing physiological aqueous solution suppressed the death of the mesenchymal stem cells (Patent Document 3). Because the damage of cells by proteolytic enzyme treatment induces a pathway of cell death (apoptosis or the like), such an effect by trehalose is probably due to the suppression of an apoptosis pathway or the promotion of the function repairing the cell damage. The present inventors have also reported that the addition of a saccharide, such as trehalose or dextran, to a suspension of mesenchymal stem cells can suppress the aggregation, and a decrease in the survival rate, of the mesenchymal stem cells when have been preserved for a short period of time (30 minutes to 6 hours) (Patent Document 4). However, it has been unclear whether or not the combined use of trehalose and dextran can synergistically suppress a decrease in the survival rate of mammalian cells, such as mesenchymal stem cells, and synergistically increase the percentage of living cells.

PRIOR ART DOCUMENTS

Patent Documents

Patent Document 1: Japanese Patent No. 3253131
Patent Document 2: International Publication No. WO 2007/043698
Patent Document 3: International Publication No. WO 2012/133575
Patent Document 4: Japanese unexamined Patent Application Publication No. 2012-115253

Non-Patent Documents

Non-patent Document 1: Gage, F. H., Science 287: 1433-1438 (2000)
Non-patent Document 2: Morrison, S. J. et al., Cell 96: 737-749 (1999)
Non-patent Document 3: Batle, E. et al., Cell 111: 251-263 (2002)
Non-patent Document 4: Lane, T. A. et al., Transfusion 49: 1471-1481 (2009)

Non-patent Document 5: Chem, F. et al., Yonsei Med. J. 45: 1107-1114 (2004)

SUMMARY OF THE INVENTION

Object to be Solved by the Invention

An object of the present invention is to provide a method for preserving mammalian cells over a long period of time using a solution for cell transplantation, capable of effectively suppressing cell death when the mammalian cells have been preserved, and the solution for cell transplantation.

Means to Solve the Object

The present inventors have reported that as described above, the short-time (30 minutes to 6 hours) preservation of mesenchymal stem cells in a solution containing a saccharide, such as trehalose or dextran, can suppress a decrease in the survival rate of the cells (Patent Document 4). However, the invention described in Patent Document 4 did not demonstrate a synergistic effect by the combined use of trehalose and dextran. In intensive studies for solving the above problem, it has been found that the preservation of human mesenchymal stem cells from bone marrow (hMSC-BM) or human peripheral blood T cells (hPBT) in a physiological aqueous solution containing trehalose and dextran to particular concentrations of 2.0 to 6.0% [w/v] and 4.0 to 7.0% [w/v], respectively can synergistically suppress a decrease in the survival rate of the cells for a long period of time (at least 14 days) and synergistically increase the percentage of living cells, thereby accomplishing the present invention.

Thus, the present invention relates to (1) a method for preserving a mammalian cell in a physiological aqueous solution for cell transplantation comprising 2.0 to 6.0% (w/v) of trehalose, a derivative thereof, or a salt of trehalose or the derivative, and 4.0 to 7.0% (w/v) of dextran, a derivative thereof or a salt of dextran or the derivative, (2) the method according to (1) above, wherein the physiological aqueous solution is selected from the group consisting of lactate Ringer's solution, saline, Ringer's solution, and acetate Ringer's solution, (3) the method according to (1) or (2) above, wherein the mammalian cell is preserved in the physiological aqueous solution for cell transplantation for 3 to 14 days, (4) the method according to any one of (1) to (3) above, wherein the mammalian cell is a mammalian mesenchymal stem cell or a mammalian T cell, and (5) the method according to (4) above, wherein the mammalian mesenchymal stem cell is a human mesenchymal stem cell from bone marrow and the mammalian T cell is a human peripheral blood T cell.

The present invention also relates to (6) a physiological aqueous solution for cell transplantation comprising 2.0 to 6.0% (w/v) of trehalose, a derivative thereof, or a salt of trehalose or the derivative, and 4.0 to 7.0% (w/v) of dextran, a derivative thereof, or a salt of dextran or the derivative, (7) the physiological aqueous solution for cell transplantation according to (6) above, wherein the physiological aqueous solution is selected from the group consisting of lactate Ringer's solution, saline, Ringer's solution, and acetate Ringer's solution, (8) the physiological aqueous solution for cell transplantation according to (6) or (7) above, wherein the mammalian cell is a mammalian mesenchymal stem cell or a mammalian T cell, and (9) the physiological aqueous solution for cell transplantation according to (8) above, wherein the mammalian mesenchymal stem cell is a human mesenchymal stem cell from bone marrow and the mammalian T cell is a human peripheral blood T cell.

The present invention also relates to (10) a physiological aqueous solution containing cells for transplantation comprising: a mammalian cell; 2.0 to 6.0% (w/v) of trehalose, a derivative thereof, or a salt of trehalose or the derivative; and 4.0 to 7.0% (w/v) of dextran, a derivative thereof or a salt of dextran or the derivative, (11) the physiological aqueous solution containing cell for transplantation according to (10) above, wherein the physiological aqueous solution is selected from the group consisting of lactate Ringer's solution, saline, Ringer's solution, and acetate Ringer's solution, (12) the physiological aqueous solution containing cell for transplantation according to (10) or (11) above, wherein the mammalian cell is a mammalian mesenchymal stem cell or a mammalian T cell, and (13) the physiological aqueous solution containing cell for transplantation according to (12) above, wherein the mammalian mesenchymal stem cell is a human mesenchymal stem cell from bone marrow and the mammalian T cell is a human peripheral blood T cell.

Other embodiments of the present invention can include a combination of a physiological aqueous solution and trehalose, a derivative thereof, or a salt of trehalose or the derivative and dextran, a derivative thereof or a salt of dextran or the derivative for preserving mammalian cells, and use of a combination of a physiological aqueous solution and trehalose, a derivative thereof, or a salt of trehalose or the derivative and dextran, a derivative thereof or a salt of dextran or the derivative for preparing a solution for transplanting mammalian cells; more specifically, the above-described trehalose, a derivative thereof, or a salt of trehalose or the derivative and dextran, a derivative thereof or a salt of dextran or the derivative are active ingredients for suppressing a decrease in the survival rate of the cells.

Effect of the Invention

According to the present invention, a decrease in the survival rate of cells including stem cells, such as mesenchymal stem cells, and leukocytes, such as T cells, can be suppressed when a suspension of the cells is preserved for a long period of time (at least 14 days); thus, a good-quality cell suspension for transplantation in regenerative medicine or cancer treatment can be provided not only to a production area for the cell suspension and its peripheral areas but also to distant places, and although a sterility test is performed for quality assurance inspection in shipping a pharmaceutical product and the sterility test takes the period of 14 days according to the Japanese Pharmacopoeia, the good-quality cell suspension can be provided even after producing the cell suspension and performing the sterility test.

BRIEF DESCRIPTION OF DRAWINGS

FIG. 1 is a graph showing the results of analyzing the cell survival rate when hMSC-BM were preserved for 14 days using each of 11 solutions for mammalian cell transplantation (S, LR, "LR+1% D", "LR+3% D", "LR+5% D", "LR+7% D", "LR+3% T", "LR+3% T+1% D", "LR+3% T+3% D", "LR+3% T+5% D", and "LR+3% T+7% D" solutions: see "1-1-1 Solution for Cell Transplantation" in Example 1). The ordinate axis shows the percentage of living cells based on the total number of the cells as the cell survival rate (%) (mean±standard deviation [n=4]). As a control, the cell survival rate before preservation in Dulbecco's phosphate buffered saline (D-PBS [-]) (hereinafter simply referred to as "PBS") solution is shown ("P" on the abscissa axis in the figure).

FIG. 2 is a graph showing the results of analyzing the cell survival rate when hMSC-BM were preserved for 3 days, 7 days, and 14 days using each of 11 solutions for mammalian cell transplantation (S, LR, "LR+1% D", "LR+3% D", "LR+5% D", "LR+7% D", "LR+3% T", "LR+3% T+1% D", "LR+3% T+3% D", "LR+3% T+5% D", and "LR+3% T+7% D" solutions ["2 to 12", respectively on the abscissa axis in the figure]: see "1-1-1 Solution for Cell Transplantation" in Example 1). The ordinate axis shows the percentage of living cells based on the total number of the cells as the cell survival rate (%) (mean±standard deviation [n=4]). As a control, the cell survival rate before preservation (0 days after preservation) in PBS solution is shown ("1" on the abscissa axis in the figure).

FIG. 3 is a graph showing the results of analyzing the cell survival rate when hMSC-BM were preserved for 14 days using each of 13 solutions for mammalian cell transplantation (S, LR, "LR+1% T", "LR+3% T", "LR+5% T", "LR+7% T", "LR+10% T", "LR+5% D", "LR+5% D+1% T", "LR+5% D+3% T", "LR+5% D+5% T", "LR+5% D+7% T", and "LR+5% D+10% T" solutions: see "2-1-1 Solution for Cell Transplantation" in Example 2). The ordinate axis shows the percentage of living cells based on the total number of the cells as the cell survival rate (%) (mean±standard deviation [n=4]). As a control, the cell survival rate before preservation in PBS solution is shown ("P" on the abscissa axis in the figure).

FIG. 4 is a graph showing the results of analyzing the cell survival rate when hMSC-BM were preserved for 3 days, 7 days, and 14 days using each of 11 solutions for mammalian cell transplantation (S, LR, "LR+1% T", "LR+3% T", "LR+5% T", "LR+7% T", "LR+5% D", "LR+5% D+1% T", "LR+5% D+3% T", "LR+5% D+5% T", and "LR+5% D+7% T" solutions ["2 to 12", respectively on the abscissa axis in the figure]: see "2-1-1 Solution for Cell Transplantation" in Example 2). The ordinate axis shows the percentage of living cells based on the total number of the cells as the cell survival rate (%) (mean±standard deviation [n=4]). As a control, the cell survival rate before preservation (0 days after preservation) in PBS solution is shown ("1" on the abscissa axis in the figure).

FIG. 5 is a graph showing the results of analyzing the cell survival rate when hMSC-BM were preserved for 14 days using each of 11 solutions for mammalian cell transplantation (S, LR, LRD, LRTD, "LRD+GL", "LRD+SR", "LRD+MN", "LRD+LC", "LRD+RF", "LRD+ML", and "LRD+SC" solutions: see "3-1-1 Solution for Cell Transplantation" in Example 3). The ordinate axis shows the percentage of living cells based on the total number of the cells as the cell survival rate (%) (mean±standard deviation [n=4]). "*" in the figure shows that a statistically significant difference (P<0.05) against LRD exists by Dunnett's test.

FIG. 6 is a graph showing the results of analyzing the cell survival rate when hMSC-BM were preserved for 14 days using each of 11 solutions for mammalian cell transplantation (S, LR, LRT, LRTD, "LRT+GL", "LRT+SR", "LRT+MN", "LRT+LC", "LRT+RF", "LRT+ML", and "LRT+SC" solutions: see "4-1-1 Solution for Cell Transplantation" in Example 4). The ordinate axis shows the percentage of living cells based on the total number of the cells as the cell survival rate (%) (mean±standard deviation [n=4]). "*" in the figure shows that a statistically significant difference (P<0.05) against LRT exists by Dunnett's test.

FIG. 7 is a graph showing the results of analyzing the cell survival rate when hMSC-BM were preserved for 14 days using each of 11 solutions for mammalian cell transplantation (S [Otsuka Normal Saline], LR [Lactec injection], LRD [5% (w/v) dextran-containing Lactec injection], LRT [3% (w/v) trehalose-containing Lactec injection], "LR+GL" [glucose-containing Lactec injection], "LR+SR" [sorbitol-containing Lactec injection], "LR+MN" [mannitol-containing Lactec injection], "LR+LC" [lactose-containing Lactec injection], "LR+RF" [raffinose-containing Lactec injection], "LR+ML" [maltose-containing Lactec injection], and "LR+SC" [sucrose-containing Lactec injection] solutions). The ordinate axis shows the percentage of living cells based on the total number of the cells as the cell survival rate (%) (mean±standard deviation [n=4]). "***" in the figure shows that a statistically significant difference (P<0.001) against LR exists by Dunnett's test.

FIG. 8 is a graph showing the results of analyzing the cell survival rate when hMSC-BM were preserved for 14 days using each of 10 solutions for mammalian cell transplantation (LR, LRTD, S, STD, 5% glucose, 5% glucose TD, Ringer, Ringer TD, Veen, and Veen TD solutions: see "5-1-1 Solution for Cell Transplantation" in Example 5). The ordinate axis shows the percentage of living cells based on the total number of the cells as the cell survival rate (%) (mean±standard deviation [n=4]). As a control, the survival rate of cells before preservation in PBS solution is shown ("P" on the abscissa axis in the figure).

FIG. 9 is a graph showing the results of analyzing the cell survival rate when hPBT were preserved for 1 day, 3 days, 7 days, and 14 days using each of 5 solutions for mammalian cell transplantation (S, LR, LRT, LRD, and LRTD). The ordinate axis shows the percentage of living cells based on the total number of the cells as the cell survival rate (%) (mean±standard deviation [n=6]). As a control, the survival rate of cells before preservation (0 days after preservation) in PBS solution is shown ("P" on the abscissa axis in the figure).

MODE OF CARRYING OUT THE INVENTION

The method for preserving mammalian cells according to the present invention is a method limited to the application of "for use in cell transplantation", which involves preserving mammalian cells in a physiological aqueous solution comprising 2.0 to 6.0% (w/v) of a trehalose and 4.0 to 7.0% (w/v) of a dextran (the present solution for cell transplantation); more specifically, the present solution for cell transplantation comprises a trehalose and a dextran as active ingredients for suppressing a decrease in the cell survival rate. The density of mammalian cells preserved in the present solution for cell transplantation is typically in the range of from $10^3$ to $10^{10}$ cells/ml.

For the present solution containing cells for transplantation, mammalian cells are typically contained in the present solution for cell transplantation. The present solution containing cells for transplantation can be prepared by adding mammalian cells to the present solution for cell transplantation, or by adding a trehalose to 2.0 to 6.0% (w/v) and a dextran to 4.0 to 7.0% (w/v) to a physiological aqueous solution containing mammalian cells.

Examples of the mammal according to the present invention can include a rodent, such as a mouse, a rat, a hamster, or a guinea pig, a lagomorpha, such as a rabbit, an ungulate, such as a pig, a cow, a goat, a horse, or a sheep, a carnivora, such as a dog or a cat, and a primate, such as a human, a monkey, a rhesus monkey, a cynomolgus monkey, a marmoset, an orangutan, or a chimpanzee; among others, preferable examples thereof can include a mouse, a pig, and a human.

The physiological aqueous solution applied to the present solution for cell transplantation and the present solution containing cells for transplantation is not particularly limited provided that it is an isotonic aqueous solution in which the concentrations of salt and sugar and the like are adjusted with sodium, potassium, and the like so as to provide almost the same osmotic pressure as that of body fluid or cell fluid. Specific examples thereof can include saline, salines having buffering effects (phosphate buffered saline [PBS], Tris buffered saline [TES], and HEPES buffered saline), Ringer's solution, lactate Ringer's solution, acetate Ringer's solution, bicarbonate Ringer's solution, a 5% glucose aqueous solution, basal media for animal cell culture (DMEM, EMEM, RPMI-1640, α-MEM, F-12, F-10, M-199 and the like), and isotonic agents (glucose, D-sorbitol, D-mannitol, lactose, sodium chloride and the like); among others, preferred is one selected from the group consisting of lactate Ringer's solution, saline, Ringer's solution, and acetate Ringer's solution; particularly preferred is lactate Ringer's solution or saline. The physiological aqueous solution can be one commercially available or of one's own preparation. Examples of the commercially available one can include Otsuka Normal Saline (from Otsuka Pharmaceutical Factory Co., Ltd.) (saline), Ringer's Solution "OTSUKA" (from Otsuka Pharmaceutical Factory Co., Ltd.) (Ringer's solution), Lactec (R) Injection (from Otsuka Pharmaceutical Factory Co., Ltd.) (lactate Ringer's solution), Veen F Infusion (from Kowa Pharmaceutical Co., Ltd.) (acetate Ringer's solution), OTSUKA GLUCOSE INJECTION 5% (from Otsuka Pharmaceutical Factory Co., Ltd.) (5% glucose aqueous solution), and Bicanate Infusion (from Otsuka Pharmaceutical Factory Co., Ltd.) (bicarbonate Ringer's solution). As used herein, the "isotonic" means having an osmotic pressure ranging from 250 to 380 mOsm/l.

The present solution for cell transplantation and the present solution containing cells for transplantation can be properly supplemented with additives, such as a stabilizer (e.g., human serum albumin or polyethylene glycol), a buffer (e.g., phosphate buffer or sodium acetate buffer), a chelating agent (e.g., EDTA, EGTA, citric acid, or salicylate), an amino acid (e.g., a nonessential amino acid, such as glutamine, alanine, asparagine, serine, aspartic acid, cysteine, glutamic acid, glycine, proline, or tyrosine), a vitamin (e.g., choline chloride, pantothenic acid, folic acid, nicotinamide, pyridoxal hydrochloride, riboflavin, thiamin hydrochloride, ascorbic acid, biotin, or inositol), a solubilizer, a preservative, and an antioxidant.

The preservation period when mammalian cells are preserved in the present solution for cell transplantation can be a time (period) enough to suppress a decrease in the cell survival rate and increase the percentage of living cells, and is, for example, 12 hours or more, 1 day or more, 2 days or more, 3 days or more, or 7 days or more. Because too long a period for preserving mammalian cells has the possibility of adversely affecting the survival of cells, the period is typically 21 days or less, preferably 16 days or less, more preferably 14 days or less in view of avoiding the adverse effect on the survival rate of cells. Thus, the preservation period is typically 12 hours to 21 days, 1 to 21 days, 2 to 21 days, 3 to 21 days, or 7 to 21 days, preferably 12 hours to 16 days, 1 to 16 days, 2 to 16 days, 3 to 16 days, or 7 to 16 days, more preferably 12 hours to 14 days, 1 to 14 days, 2 to 14 days, 3 to 14 days, or 7 to 14 days, most preferably 3 to 14 days. The suppression of death of mammalian cells preserved in the present solution for cell transplantation can be confirmed by a known method capable of detecting cell death, such as a Trypan Blue staining method, TUNEL method, Nexin method, or FLICA method.

The preservation temperature when mammalian cells are preserved in the present solution for cell transplantation can be a temperature at which the solution for cell transplantation is not frozen and the cells are viable, and is in the range of typically from 0 to 37° C., preferably from 0 to 25° C. (room temperature).

Examples of trehalose as a trehalose as described above can include α,β-trehalose as a disaccharide in which α-glucose and β-glucose molecules are 1,1-glycoside-linked and β,β-trehalose as a disaccharide in which 2 β-glucose molecules are 1,1-glycoside-linked, in addition to α,α-trehalose as a disaccharide in which 2 α-glucose molecules are 1,1-glycoside-linked; among others, α,α-trehalose is preferable. These trehaloses can be produced by any of the known methods, such as chemical synthesis, production by a microorganism, and production by an enzyme; however, commercially available ones can also be used. Examples thereof can include α,α-trehalose (from Hayashibara Co., Ltd.) and α,α-trehalose (from Wako Pure Chemical Industries Ltd.).

The trehalose derivative as a trehalose as described above is not particularly limited provided that it is one of glycosyltrehaloses in which one or more saccharide units are bonded to trehalose as a disaccharide; the glycosyltrehaloses include glycosyltrehalose, maltosyltrehalose, and maltotriosyltrehalose.

Examples of the salt of trehalose or its derivative as a trehalose as described above can include an acid addition salt, such as a hydrochloride, a hydrobromate, a hydroiodide, a phosphate, a nitrate, a sulfate, an acetate, a propionate, a toluenesulfonate, a succinate, an oxalate, a lactate, a tartrate, a glycolate, a methanesulfonate, a butyrate, a valerate, a citrate, a fumarate, a maleate, and a malate; a metal salt, such as a sodium salt, a potassium salt, and a calcium salt; an ammonium salt; and an alkylammonium salt. These salts are each used in the form of a solution at the time of use, and their action preferably has the same potency as that of trehalose. These salts can form hydrates or solvates, and can be used alone or in a proper combination of two or more thereof.

Dextran as a dextran as described above is not particularly limited provided that it is a polysaccharide $(C_6H_{10}O_5)_n$ consisting of D-glucose, using a 1→6 bonding as the main chain, and examples thereof can include dextran (weight average molecular weight (Mw)=40,000) and dextran 70 (Mw=70,000). These dextrans can be produced by any of the known methods, such as chemical synthesis, production by a microorganism, and production by an enzyme; however, commercially available ones can also be used. Examples thereof can include commercial products, such as Low Molecular Weight Dextran L Injection (from Otsuka Pharmaceutical Factory Co., Ltd.) and Dextran 70 (from Tokyo Kasei Kogyo Co., Ltd.).

Examples of the dextran derivative as a dextran as described above include dextran sulfate, carboxylated dextran, and diethylaminoethyl (DEAE)-dextran.

Examples of the salt of dextran and its derivative as a dextran as described above can include an acid addition salt, such as a hydrochloride, a hydrobromate, a hydroiodide, a phosphate, a nitrate, a sulfate, an acetate, a propionate, a toluenesulfonate, a succinate, an oxalate, a lactate, a tartrate, a glycolate, a methanesulfonate, a butyrate, a valerate, a citrate, a fumarate, a maleate, and a malate; a metal salt, such as a sodium salt, a potassium salt, and a calcium salt; an ammonium salt; and an alkylammonium salt. These salts are each used in the form of a solution at the time of use, and their action preferably has the same potency as that of dextran. These salts can form hydrates or solvates, and can be used alone or in a proper combination of two or more thereof.

Examples of the mammalian cells according to the present invention can include mammalian pancreatic islet cells intravenously administered to patients with type I diabetes, and mammalian dendritic cells, natural killer (NK) cells, T cells (e.g., alpha beta ($\alpha\beta$) T cells, gamma delta ($\gamma\delta$) T cells, cytotoxic T lymphocytes (CTL), and helper T cells), macrophage, and leukocytes (e.g., neutrophils and eosinophils) intravenously administered to cancer patients in addition to mammalian stem cells administered via the blood vessel for regenerative medicine or the like; preferred are T cells. These cells can be isolated by known common methods. For example, leukocytes, T cells, helper T cells, cytotoxic T cells, and $\gamma\delta$ cells can be isolated from a sample of the hemolysis-treated peripheral blood or cord blood using a fluorescent-activated cell sorter (FACS) using antibodies to a leukocyte cell surface marker (CD45), a T cell surface marker (CD3), a helper T cell surface marker (CD4), a cytotoxic T cell (CD8), and a $\gamma\delta$ T cell surface marker (CD39) or an automatic magnetic cell separation apparatus (autoMACS) using antibodies to the cell surface markers labeled with a labeling substance, such as a fluorescent substance, biotin, or avidin, and a MACS bead (magnetic bead)-conjugated antibody to the labeling substance. Examples of the labeling substance can include allophycocyanin (APC), phycoerythrin (PE), FITC (fluorescein isothiocyanate), Alexa Fluor 488, Alexa Fluor 647, Alexa Fluor 700, PE-Texas Red, PE-Cy5, and PE-Cy7.

The "stem cells" means immature cells having self-renewal potential and differentiation/proliferation potential. Stem cells include a subpopulation, such as pluripotent stem cells, multipotent stem cells, or unipotent stem cells, according to differentiation ability. The pluripotent stem cells mean cells which, as such, cannot become an individual organism but has a capability capable of differentiating into all tissues or cells constituting a living body. The multipotent stem cells mean a cell having a capability capable of differentiating into a plurality of, but not all, types of tissues or cells. The unipotent stem cells mean cells having a capability capable of differentiating into a particular tissue or cell.

Examples of the pluripotent stem cells can include embryonic stem cells (ES cells), EG cells, and iPS cells. ES cells can be produced by culturing an inner cell mass on feeder cells or in a medium containing LIF. The method for producing ES cells is described, for example, in WO 96/22362, WO 02/101057, U.S. Pat. Nos. 5,843,780, 6,200,806, or U.S. Pat. No. 6,280,718. EG cells can be produced by culturing primordial germ cells in a medium containing mSCF, LIF, and bFGF (Cell, 70: 841-847, 1992). iPS cells can be produced by introducing reprogramming factors, such as Oct3/4, Sox2, Klf4 (and optionally further c-Myc or n-Myc), into somatic cells (for example, fibroblasts, or skin cells) (Cell, 126: p. 663-676, 2006; Nature, 448: p. 313-317, 2007; Nat. Biotechnol, 26; p. 101-106, 2008; Cell 131: p. 861-872, 2007; Science, 318: p. 1917-1920, 2007; Cell Stem Cells 1: p. 55-70, 2007; Nat. Biotechnol, 25: p. 1177-1181, 2007; Nature, 448: p. 318-324, 2007; Cell Stem Cells 2: p. 10-12, 2008; Nature 451: p. 141-146, 2008; Science, 318: p. 1917-1920, 2007). Stem cells established by culturing early embryos made by transplanting the nucleus of somatic cells are also preferable as pluripotent stem cells (Nature, 385, 810 (1997); Science, 280, 1256 (1998); Nature Biotechnology, 17, 456 (1999); Nature, 394, 369 (1998); Nature Genetics, 22, 127 (1999); Proc. Natl. Acad. Sci. USA., 96, 14984 (1999)), and Rideout III et al. (Nature Genetics, 24, 109 (2000)).

Examples of the multipotent stem cells include mesenchymal stem cells capable of differentiating into cells, such as an adipocyte, an osteocyte, a chondrocyte, and an adipocyte, hematopoietic progenitors capable of differentiating into hematocytic cells, such as a leucocyte, an erythrocyte, and a platelet, neural stem cells capable of differentiating into cells, such as a neuron, an astrocyte, and an oligodendrocyte, and somatic stem cells, such as a myeloid stem cell and a germ stem cell. The multipotent stem cells are preferably mesenchymal stem cells. The mesenchymal stem cells mean stem cells capable of differentiating into all or some of an osteoblast, a chondroblast, and a lipoblast. The multipotent stem cells can be isolated from a living body by methods known per se. For example, the mesenchymal stem cells can be collected from the bone marrow, fat tissue, peripheral blood, cord blood, and the like of mammals by known general methods. For example, human mesenchymal stem cells can be isolated by culturing and subculturing hematopoietic stem cells or the like after bone marrow puncture (Journal of Autoimmunity, 30 (2008) 163-171). Multipotent stem cells can also be obtained by culturing the above-described pluripotent stem cells under suitable induction conditions. The mesenchymal stem cells are preferably mesenchymal stem cells derived from human bone marrow.

Examples of the mammalian cells according to the present invention can include adherent cells. As used herein, the "adherent" cells mean scaffold-dependent cells capable of surviving, proliferating, and producing substances by adhering to the scaffold. Examples of the adherent stem cells can include pluripotent stem cells, mesenchymal stem cells, neural stem cells, myeloid stem cells, and germ stem cells. The adherent stem cells are preferably mesenchymal stem cells or pluripotent stem cells.

The mammalian cells (population) according to the present invention can be those separated from a living body or those subcultured in vitro; however, they are preferably those isolated or purified. As used herein, the "isolated or purified" means that the operation of removing components other than a desired component has been applied. The purity of the isolated or purified mammalian cells (the percentage of desired cells, such as mammalian stem cells, based on the total number of cells) is typically 30% or more, preferably 50% or more, more preferably 70% or more, still more preferably 90% or more (for example, 100%).

The mammalian cells (population) preserved in the present solution for cell transplantation are preferably in a single-cell state. As used herein, the "single cell state" means that cells do not get together with other cells to form a mass (in other words, an unaggregated state). The mammalian cells in a single-cell state can be prepared by subjecting mammalian cells cultured in vitro to enzyme treatment with trypsin/EDTA or the like. The percentage of the mammalian cells in a single-state in the mammalian cells is typically 70% or more, preferably 90% or more, more preferably 95% or more, still more preferably 99% or more (for example, 100%). The percentage of the cells in a single state can be determined by dispersing the mammalian cells in PBS, observing the dispersion under a microscope, and examining a plurality of (e.g., 1,000) randomly selected cells for the presence of aggregation.

The mammalian cells (population) preserved in the present solution for cell transplantation are preferably floating.

As used herein, the "floating" refers to that cells are held in the solution for transplantation without contacting with the inner wall of a container housing the solution for transplantation.

When the mammalian cells preserved in the present solution for cell transplantation aggregate or precipitate, the cells are preferably suspended before transplantation by a method well-known in the art, such as pipetting or tapping.

The present invention will be more specifically described below with reference to Examples. However, these Examples are not intended to limit the technical scope of the present invention.

EXAMPLES

Example 1

1. Confirmation 1 of that Present Solution for Cell Transplantation has Synergistic Effect of Suppressing Decrease in Cell Survival Rate. (Evaluation of Relation Between Change in Dextran Concentration and Synergistic Effect at Fixed Trehalose Concentration of 3% (w/v))
1-1 Material
1-1-1 Solution for Cell Transplantation
S: Otsuka Normal Saline (from Otsuka Pharmaceutical Factory Co., Ltd.)
LR: Lactec (R) injection (from Otsuka Pharmaceutical Factory Co., Ltd.)
LR+1% D: a 1% (w/v) dextran-containing Lactec injection
LR+3% D: a 3% (w/v) dextran-containing Lactec injection
LR+5% D: a 5% (w/v) Dextran-containing Lactec injection
LR+7% D: a 7% (w/v) Dextran-containing Lactec injection
LR+3% T: a 3% (w/v) Trehalose-containing Lactec injection
LR+3% T+1% D: a 3% (w/v) trehalose- and 1% (w/v) dextran-containing Lactec injection
LR+3% T+3% D: a 3% (w/v) trehalose- and 3% (w/v) dextran-containing Lactec injection LR+3% T+5% D: a 3% (w/v) trehalose- and 5% (w/v) dextran-containing Lactec injection LR+3% T 7% D: a 3% (w/v) trehalose- and 7% (w/v) dextran-containing Lactec injection
1-1-2 Preparation of Solution for Cell Transplantation 1) The 3% (w/v) trehalose-containing Lactec injection ("LR+3% T" solution) was prepared by adding and dissolving trehalose (from Hayashibara Co., Ltd.) in the Lactec injection (LR solution).

2) A 3% (w/v) trehalose- and 10% (w/v) dextran-containing Lactec injection ("LR+3% T+10% D" solution) was prepared by adding and dissolving trehalose (from Hayashibara Co., Ltd.) in Low Molecular Dextran L Injection (10% [w/v] dextran-containing Lactec injection) (from Otsuka Pharmaceutical Factory Co., Ltd.) ("LR+10% D" solution).

3) The Lactec injections containing predetermined concentrations (1, 3, 5, and 7% [w/v]) of dextran ("LR+1, 3, 5, and 7% D" solutions) were prepared by diluting the "LR+10% D" solution with the LR solution.

4) The Lactec injections containing 3% (w/v) trehalose and predetermined concentrations (1, 3, 5, and 7% [w/v]) of dextran ("LR+3% T+1, 3, 5, and 7% D" solutions) were prepared by diluting the "LR+3% T+10% D" solution with the "LR+3% T" solution.
1-1-3 Preparation of Mammalian Cell Human mesenchymal stem cells from bone marrow [hMSC-BM] (from Lonza Co., Ltd.) were prepared according the procedures described in [1] to [8] below and used in the present experiment.

[1] hMSC-BM were cultured in a 5% $CO_2$ incubator at 37° C. in the presence of a medium kit specific for human mesenchymal stem cells (from Lonza Co., Ltd.) (hereinafter referred to as "MSC medium") using a 75-cm² flask. The state of the cells was observed under a microscope, and culture was performed until a confluent state of about 80% was reached.

[2] The MDC medium was removed using an aspirator, and hMSC-BM were rinsed with 8 mL/flask of PBS (from Invitrogen Co., Ltd.).

[3] PBS was removed using an aspirator, and 3.75 mL/flask of trypsin-EDTA (from Lonza Co., Ltd.) was added, followed by standing at room temperature for 5 minutes.

[4] Swing was carried out in a slow manner while hMSC-BM were observed under a microscope until about 90% thereof were detached.

[5] 3.75 mL/Flask of the MSC medium was added to stop the trypsin reaction, and hMSC-BM were recovered by pipetting and transferred to a 50-mL centrifuge tube.

[6] Centrifugation was carried out at 600×g and 25° C. for 5 minutes.

[7] The MSC medium as the supernatant was removed using an aspirator, and 4 mL/flask of PBS (from Invitrogen Co., Ltd.) was added, followed by suspending an hMSC-BM pellet (precipitate).

[8] 10 μL of the hMSC-BM suspension was taken; the number of the cells was measured using a cell counter; and PBS (from Invitrogen Co., Ltd.) was added thereto to 5×10⁵ cells/mL, which was then cooled with ice.
1-2 Method To confirm that the present solution for cell transplantation had a synergistic effect of suppressing a decrease in the cell survival rate, an experiment was carried out according to the procedures described in [1] to [3] below.

[1] The hMSC-BM suspension prepared in the step [7] of the "1-1-3 Preparation of Mammalian Cell" described above was dispensed into a 15-mL conical centrifuge tube using FINPIPETTE (100 to 1,000 μL) and centrifuged at 600×g and 25° C. for 5 minutes.

[2] The supernatant after centrifugation treatment was aspirated/removed, and the resultant was suspended in each of the 11 solutions for cell transplantation and then preserved in a refrigerator (under conditions of 4° C.) for days. To measure the cell survival rate before preservation, the supernatant after centrifugation treatment was aspirated/removed, and the resultant was then suspended in PBS (from Invitrogen Co., Ltd.), immediately followed by taking a portion (20 μL) of the suspension, mixing the portion with 20 μL of Trypan blue stain solution (from Gibco Co., Ltd.), and then measuring the total number of the cells and the number of dead cells using a cell counter under a microscope to evaluate the rate of living cells (see "P" in FIG. 1).

[3] After preserving hMSC-BM in the solution for cell transplantation for 14 days, stirring (5 times pipetting at a liquid volume of 500 μL) was gently performed in a state in which the end of a tip was inserted to a position visually at on the order of 5 mm from the bottom to make cells in a suspended state, and a portion (20 μL) of the suspension was taken into a 1.5-mL microtube, mixed with 20 μL of Trypan blue stain solution (from Gibco Co., Ltd.), and then measured for the total number of the cells and the number of dead cells using a cell counter under a microscope to evaluate the rate of living cells.
1-3 Result The results of evaluating the rate of living cells are shown in Table 1 and FIG. 1. When hMSC-BM were preserved in the S solution and the LR solution, few surviving hMSC-BM were observed (less than 1% for the S solution and 1% for the LR solution), whereas when hMSC-BM were preserved in the "LR+1, 3, 5, and 7% D" solutions, the percentage of surviving hMSC-BM increased to 4%, 9%, 12%, and 20%, respectively (Table 1 and FIG. 1). When hMSC-BM were preserved in the "LR+3% T" solution, the percentage of surviving hMSC-BM also increased to 4% (Table 1 and FIG. 1). These results show that although the long-term preservation of mammalian cells, such as hMSC-BM, in saline or a physiological aqueous solution, such as lactate Ringer's solution, results in the death of most cells, the use of a physiological aqueous solution containing dextran or trehalose can suppress the cell death and can increase the percentage of living cells.

When hMSC-BM were preserved in the "LR+3% T+1, 3, 5, and 7% D" solutions, the percentage of surviving hMSC-BM was 11%, 33%, 57%, and 50%, respectively and increased compared to that when hMSC-BM were preserved in the "LR+3% T" solution (Table 1 and FIG. 1). In addition, the cell survival rates when the "LR+3% T" and "LR+1% D" solutions were used were each 4%, totaling 8%, whereas the cell survival rate when the "LR+3% T+1% D" solution was used was as high as 11% (1.4 times). Similarly, the values of the cell survival rates when the "LR+3% T" and "LR+3% D" solutions were used totaled 13%, whereas the cell survival rate when the "LR+3% T+3% D" solution was used was as high as 33% (2.5 times); the values of the cell survival rates when the "LR+3% T" and "LR+5% D" solutions were used totaled 16%, whereas the cell survival rate when the "LR+3% T+5% D" solution was used was as high as 57% (3.6 times); and the values of the cell survival rates when the "LR+3% T" and "LR+7% D" solutions were used totaled 24%, whereas the cell survival rate when the "LR+3% T+7% D" solution was used was as high as 50% (2.1 times). These results show that the combined use of 3% trehalose and around 5% (4 to 7%) dextran can synergistically suppress a decrease in the cell survival rate when mammalian cells, such as hMSC-BM, were preserved for a long period of time and can synergistically increase the percentage of living cells.

TABLE 1

| Survival Rate (%) of Cell When Preserved for 14 Days | |
|---|---|
| Solution for Cell Transplantation | Cell Survival Rate (%) |
| S | 0 ± 1 |
| LR | 1 ± 1 |
| LR + 1% D | 4 ± 4 |
| LR + 3% D | 9 ± 3 |
| LR + 5% D | 12 ± 2 |
| LR + 7% D | 20 ± 7 |
| LR + 3% T | 4 ± 1 |
| LR + 3% T + 1% D | 11 ± 3 |
| LR + 3% T + 3% D | 33 ± 7 |
| LR + 3% T + 5% D | 57 ± 11 |
| LR + 3% T + 7% D | 50 ± 17 |

For "Cell Survival Rate (%)" in the above table, the percentage of living cells based on the total number of cells is shown as the cell survival rate (%) (mean±standard deviation, [n=4]. The cell survival rate before preservation was "93±2(%)". For the 11 types of the "Solution for Cell Transplantation" in the above table, see "1-1-1 Solution for Cell Transplantation" in Example 1.

Further, the period of the preservation of hMSC-BM in the solution for cell transplantation was studied for 3 days and 7 days in addition to 14 days. The results are shown in FIG. 2. Similar to when hMSC-BM were preserved for 14 days, it was demonstrated that the combined use of 3% trehalose and around 5% (4 to 7%) dextran could also synergistically suppress a decrease in the cell survival rate when hMSC-BM were preserved for a long period of time and synergistically increase the percentage of living cells even when hMSC-BM were preserved for 3 days or 7 days.

Example 2

2. Confirmation 2 of that Present Solution for Cell Transplantation has Synergistic Effect of Suppressing Decrease in Survival Rate (Evaluation of Relation Between Change in Trehalose Concentration and Synergistic Effect at Fixed Dextran Concentration of 5% (w/v))

2-1 Material
2-1-1 Solution for Cell Transplantation
S: Otsuka Normal Saline (from Otsuka Pharmaceutical Factory Co., Ltd.)
LR: Lactec injection (from Otsuka Pharmaceutical Factory Co., Ltd.)
LR+1% T: a 1% (w/v) trehalose-containing Lactec injection
LR+3% T: a 3% (w/v) trehalose-containing Lactec injection
LR+5% T: a 5% (w/v) trehalose-containing Lactec injection
LR+7% T: a 7% (w/v) trehalose-containing Lactec injection
LR+10% T: a 10% (w/v) trehalose-containing Lactec injection
LR+5% D: a 5% (w/v) dextran-containing Lactec injection
LR+5% D+1% T: a 5% (w/v) dextran- and 1% (w/v) trehalose-containing Lactec injection
LR+5% D+3% T: a 5% (w/v) dextran- and 3% (w/v) trehalose-containing Lactec injection
LR+5% D+5% T: a 5% (w/v) dextran- and 5% (w/v) trehalose-containing Lactec injection
LR+5% D+7% T: a 5% (w/v) dextran- and 7% (w/v) trehalose-containing Lactec Injection
LR+5% D+10% T: a 5% (w/v) dextran- and 10% (w/v) trehalose-containing Lactec injection
2-1-2 Preparation of Solution for Cell Transplantation
1) The 5% (w/v) dextran-containing Lactec injection ("LR+5% D" solution) was prepared by diluting Low Molecular Weight Dextran L Injection (10% [w/v] dextran-containing Lactec injection) (from Otsuka Pharmaceutical Factory Co., Ltd.) ("LR+10% D" solution) with the Lactec Injection (LR solution).
2) The 10% (w/v) trehalose-containing Lactec injection ("LR+10% T" solution) was prepared by adding and dissolving trehalose (from Hayashibara Co., Ltd.) in the LR solution.
3) The 5% (w/v) dextran- and 10% (w/v) trehalose-containing Lactec injection ("LR+5% D+10% T" solution) was prepared by adding and dissolving trehalose (from Hayashibara Co., Ltd.) in the "LR+5% D" solution.
4) The Lactec Injections containing predetermined concentrations (1, 3, 5, and 7% [w/v]) of trehalose ("LR+1, 3, 5, and 7% T" solutions) were prepared by diluting the "LR+10% T" solution with the LR solution.
5) The Lactec Injections containing 5% (w/v) dextran and predetermined concentrations (1, 3, 5, and 7% [w/v]) of trehalose ("LR+5% D+1, 3, 5, and 7% T" solutions) were prepared by diluting the "LR+5% D+10% T" solution with the "LR+5% D" solution.
2-2 Result
After preparing hMSC-BM by the method described in "1-1-3 Preparation of Mammalian Cell" in Example 1, an experiment was performed according to the procedures described in "1-2 Method" in Example 1 using the 13 solutions for cell transplantation. The results are shown in Table 2 and FIG. 3. As in the results of Example 1, when hMSC-BM were preserved in the S solution and the LR solution, few or no surviving hMSC-BM were observed (1% for the S solution and 0% for the LR solution). When hMSC-BM were preserved in the "LR+1, 3, 5, 7, and 10% T" solutions, the percentages of living hMSC-BM were 2%, 6%, 7%, 5%, and 3%, respectively, whereas when hMSC-BM were preserved in the "LR+5% D+1, 3, 5, 7, and 10% T" solutions, the percentages of living hMSC-BM were 30%, 48%, 49%, 30%, and 14%, respectively, showing substantial increases (Table 2 and FIG. 3). Particularly, the cell survival rates when the "LR+5% D" and "LR+1% T" solutions were used were 11% and 2%, respectively, totaling 13%, whereas the cell survival rate when the "LR+5% D+1% T" solution was used was as high as 30% (2.3 times). Similarly, the values of the cell survival rates when the "LR+5% D" and "LR+3% T" solutions were used totaled 17%, whereas the cell survival rate when "LR+5% D+3% T" solution was used was as high as 48% (2.8 times); the values of the cell survival rates when the "LR+5% D" and "LR+5% T" solutions were used totaled 18%, whereas the cell survival rate when "LR+5% D+5% T" solution was used was as high as 49% (2.7 times); and the values of the cell survival rates when the "LR+5% D" and "LR+7% T" solutions were used totaled 16%, whereas the cell survival rate when "LR+5% D+7% T" solution was used was as high as 30% (1.9 times). These results show that the combined use of around 3% (2 to 6%) trehalose and 5% dextran can synergistically suppress a decrease in the cell survival rate when mammalian cells, such as hMSC-BM, are preserved for a long period of time and can synergistically increase the percentage of living cells.

TABLE 2

Survival Rate (%) of Cell When Preserved for 14 Days

| Solution for Cell Transplantation | Cell Survival Rate (%) |
| --- | --- |
| S | 1 ± 1 |
| LR | 0 ± 0 |
| LR + 1% T | 2 ± 1 |
| LR + 3% T | 6 ± 2 |
| LR + 5% T | 7 ± 2 |
| LR + 7% T | 5 ± 3 |
| LR + 10% T | 3 ± 2 |
| LR + 5% D | 11 ± 4 |
| LR + 5% D + 1% T | 30 ± 5 |
| LR + 5% D + 3% T | 48 ± 3 |
| LR + 5% D + 5% T | 49 ± 4 |
| LR + 5% D + 7% T | 30 ± 7 |
| LR + 5% D + 10% T | 14 ± 5 |

For "Cell Survival Rate (%)" in the above table, the percentage of living cells based on the total number of cells is shown as the cell survival rate (%) (mean±standard deviation, [n=4]). The cell survival rate before preservation was "95±2(%)". For the 13 types of the "Solution for Cell Transplantation" in the above table, see "2-1-1 Solution for Cell Transplantation" in Example 2.

In addition, the period of the preservation of hMSC-BM in the solution for cell transplantation was studied for 3 days and 7 days in addition to 14 days. The results are shown in FIG. 4. Similar to when hMSC-BM were preserved for 14 days, it was demonstrated that the combined use of around 3% (2 to 6%) trehalose and 5% dextran could also synergistically suppress a decrease in the cell survival rate when hMSC-BM were preserved for a long period of time and synergistically increase the percentage of living cells even when hMSC-BM were preserved for 3 days or 7 days.

Summarizing the results of Examples 1 and 2, it was demonstrated that the combined use of around 3% (2 to 6%) trehalose and around 5% (4 to 7%) dextran could synergistically suppress a decrease in the cell survival rate when mammalian cells, such as hMSC-BM, were preserved for a long period of time (at least 14 days) and could synergistically increase the percentage of living cells.

Example 3

3. Study on Effect of Suppressing Decrease in Cell Survival Rate when Solution for Cell Transplantation Having Combination of Dextran and Another Saccharide is Used 3-1 Material 3-1-1 Solution for Cell Transplantation S: Otsuka Normal Saline (from Otsuka Pharmaceutical Factory Co., Ltd.)

LR: Lactec injection (from Otsuka Pharmaceutical Factory Co., Ltd.)

LRD: a 5% (w/v) dextran-containing Lactec injection

LRTD: a 3% (w/v) trehalose- and 5% (w/v) dextran-containing Lactec injection

LRD+GL: a 5% (w/v) dextran- and 1.6% (w/v) glucose-containing Lactec injection

LRD+SR: a 5% (w/v) dextran- and 1.6% (w/v) sorbitol-containing Lactec injection

LRD+MN: a 5% (w/v) dextran- and 1.6% (w/v) mannitol-containing Lactec injection

LRD+LC: a 5% (w/v) dextran- and 3.0% (w/v) lactose-containing Lactec injection

LRD+RF: a 5% (w/v) dextran- and 4.8% (w/v) raffinose-containing Lactec injection LRD+ML: a 5% (w/v) dextran- and 3.0% (w/v) maltose-containing Lactec injection LRD+SC: a 5% (w/v) dextran- and 3.0% (w/v) sucrose-containing Lactec injection 3-1-2 Preparation of Solution for Cell Transplantation 1) The 5% (w/v) dextran-containing Lactec injection ("LRD" solution) and the 3% (w/v) trehalose- and 5% (w/v) dextran-containing Lactec injection ("LRTD" solution) were prepared according to the method described in "1-1-2 Preparation of Solution for Cell Transplantation" in Example 1.

2) The 5% (w/v) dextran- and 1.6% (w/v) glucose-containing Lactec injection ("LRD+GL" solution) was prepared by adding and dissolving glucose (from Wako Pure Chemical Industries Ltd.) in the "LRD" solution.

3) The 5% (w/v) dextran- and 1.6% (w/v) sorbitol-containing Lactec injection ("LRD+SR" solution) was prepared by adding and dissolving sorbitol (from Wako Pure Chemical Industries Ltd.) in the "LRD" solution.

4) The 5% (w/v) dextran- and 1.6% (w/v) mannitol-containing Lactec injection ("LRD+MN" solution) was prepared by adding and dissolving mannitol (from Wako Pure Chemical Industries Ltd.) in the "LRD" solution.

5) The 5% (w/v) dextran- and 3.0% (w/v) lactose-containing Lactec injection ("LRD+LC" solution) was prepared by adding and dissolving lactose (from Wako Pure Chemical Industries Ltd.) in the "LRD" solution.

6) The 5% (w/v) dextran- and 4.8% (w/v) raffinose-containing Lactec injection ("LRD+RF" solution) was prepared by adding and dissolving raffinose (from Wako Pure Chemical Industries Ltd.) in the "LRD" solution.

7) The 5% (w/v) dextran- and 3.0% (w/v) maltose-containing Lactec injection ("LRD+ML" solution) was prepared by adding and dissolving maltose (from Wako Pure Chemical Industries Ltd.) in the "LRD" solution.

8) The 5% (w/v) dextran- and 3.0% (w/v) sucrose-containing Lactec injection ("LRD+SC" solution) was prepared by adding and dissolving sucrose (from Wako Pure Chemical Industries Ltd.) in the "LRD" solution. The 7 saccharides (glucose, sorbitol, mannitol, lactose, raffinose, maltose, and sucrose) were subjected to concentration adjustment so that they have the same osmotic pressure as that of 3% (w/v) trehalose.

3-2 Result

After preparing hMSC-BM by the method described in "1-1-3 Preparation of Mammalian Cell" in Example 1, an experiment was performed according to the procedures described in "1-2 Method" in Example 1 using the 11 solutions for cell transplantation. The results are shown in FIG. 5. As in the results of Examples 1 and 2, the combined use of trehalose and dextran was shown to synergistically suppress a decrease in the cell survival rate when hMSC-BM were preserved for 14 days and increase the rate of living cells (comparison of "LRTD" with "LRD", "LR", or "S" in FIG. 5). On the other hand, the combined use of dextran with each of the 7 saccharides (glucose, sorbitol, mannitol, lactose, raffinose, maltose, and sucrose) in place of trehalose little changed the cell survival rate compared to the use of dextran alone (comparison of "LRD" with "LRD+GL", "LRD+SR", "LRD+MN", "LRD+LC", "LRD+RF", "LRD+ML", or "LRD+SC" in FIG. 5). These results show that unlike trehalose, the saccharides have not the effect of suppressing cell death when mammalian cells, such as hMSC-BM, have been preserved for a long period of time and increasing the rate of living cells in the solution for cell transplantation.

Example 4

4. Study on Effect of Suppressing Decrease in Cell Survival Rate when Solution for Cell Transplantation Having Combination of Trehalose and Another Saccharide is Used 4-1 Material 4-1-1 Solution for Cell Transplantation S: Otsuka Normal Saline (from Otsuka Pharmaceutical Factory Co., Ltd.)
LR: Lactec injection (from Otsuka Pharmaceutical Factory Co., Ltd.)
LRT: a 3% (w/v) trehalose-containing Lactec injection
LRTD: a 3% (w/v) trehalose- and 5% (w/v) dextran-containing Lactec injection
LTD+GL: a 3% (w/v) trehalose- and 1.6% (w/v) glucose-containing Lactec injection
LTD+SR: a 3% (w/v) trehalose- and 1.6% (w/v) sorbitol-containing Lactec injection
LTD+MN: a 3% (w/v) trehalose- and 1.6% (w/v) mannitol-containing Lactec injection
LTD+LC: a 3% (w/v) trehalose- and 3.0% (w/v) lactose-containing Lactec injection
LTD+RF: a 3% (w/v) trehalose- and 4.8% (w/v) raffinose-containing Lactec injection
LTD+ML: a 3% (w/v) trehalose- and 3.0% (w/v) maltose-containing Lactec injection
LTD+SC: a 3% (w/v) trehalose- and 3.0% (w/v) sucrose-containing Lactec injection 4-1-2 Preparation of Solution for Cell Transplantation 1) The 3% (w/v) trehalose-containing Lactec injection ("LRT" solution) and the 3% (w/v) trehalose- and 5% (w/v) dextran-containing Lactec injection ("LRTD" solution) were prepared according to the method described in "1-1-2 Preparation of Solution for Cell Transplantation" in Example 1.

2) The 3% (w/v) trehalose- and 1.6% (w/v) glucose-containing Lactec injection ("LRD+GL" solution) was prepared by adding and dissolving glucose (from Wako Pure Chemical Industries Ltd.) in the "LRT" solution.

3) The 3% (w/v) trehalose- and 1.6% (w/v) sorbitol-containing Lactec injection ("LRT+SR" solution) was prepared by adding and dissolving sorbitol (from Wako Pure Chemical Industries Ltd.) in the "LRT" solution.

4) The 3% (w/v) trehalose- and 1.6% (w/v) mannitol-containing Lactec injection ("LRT+MN" solution) was prepared by adding and dissolving mannitol (from Wako Pure Chemical Industries Ltd.) in the "LRT" solution.

5) The 3% (w/v) trehalose- and 3.0% (w/v) lactose-containing Lactec injection ("LRT+LC" solution) was prepared by adding and dissolving lactose (from Wako Pure Chemical Industries Ltd.) in the "LRT" solution.

6) The 3% (w/v) trehalose- and 4.8% (w/v) raffinose-containing Lactec injection ("LRT+RF" solution) was prepared by adding and dissolving raffinose (from Wako Pure Chemical Industries Ltd.) in the "LRT" solution.

7) The 3% (w/v) trehalose- and 3.0% (w/v) maltose-containing Lactec injection ("LRT+ML" solution) was prepared by adding and dissolving maltose (from Wako Pure Chemical Industries Ltd.) in the "LRT" solution.

8) The 3% (w/v) trehalose- and 3.0% (w/v) sucrose-containing Lactec injection ("LRT+SC" solution) was prepared by adding and dissolving sucrose (from Wako Pure Chemical Industries Ltd.) in the "LRT" solution. The 7 saccharides (glucose, sorbitol, mannitol, lactose, raffinose, maltose, and sucrose) were subjected to concentration adjustment so that they have the same osmotic pressure as that of 5% (w/v) dextran.

4-2 Result

After preparing hMSC-BM by the method described in "1-1-3 Preparation of Mammalian Cell" in Example 1, an experiment was performed according to the procedures described in "1-2 Method" in Example 1 using the 11 solutions for cell transplantation. The results are shown in FIG. 6. As in the results of Examples 1 to 3, the combined use of dextran and trehalose was shown to synergistically suppress a decrease in the cell survival rate when the cells were preserved for 14 days and increase the rate of living cells (comparison of "LRTD" with "LRT", "LR", or "S" in FIG. 6). On the other hand, the combined use of trehalose with each of the 7 saccharides (glucose, sorbitol, mannitol, lactose, raffinose, maltose, and sucrose) in place of dextran little changed the cell survival rate compared to the use of trehalose alone (comparison of "LRT" with "LRT+GL", "LRT+SR", "LRT+MN", "LRT+LC", "LRT+RF", "LRT+ML", or "LRT+SC" in FIG. 6). These results show that unlike dextran, the 7 saccharides have not the effect of suppressing cell death when mammalian cells, such as hMSC-BM, have been preserved for a long period of time and increasing the rate of living cells in the solution for cell transplantation.

In addition, an experiment when each of the 7 saccharides (glucose, sorbitol, mannitol, lactose, raffinose, maltose, and sucrose) was used alone without combination with trehalose or dextran was performed to confirm that the 7 saccharides had not the effect of suppressing cell death when mammalian cells, such as hMSC-BM, were preserved for a long period of time and increasing the rate of living cells in the solution for cell transplantation (FIG. 7).

Example 5

5. Study on Physiological Aqueous Solution in Present Solution for Cell Transplantation
5-1 Material
5-1-1 Solution for Cell Transplantation
LR: Lactec injection (from Otsuka Pharmaceutical Factory Co., Ltd.)
LRTD: a 3% (w/v) trehalose- and 5% (w/v) dextran-containing Lactec injection
S: Otsuka Normal Saline (from Otsuka Pharmaceutical Factory Co., Ltd.)
STD: 3% (w/v) trehalose- and 5% (w/v) Dextran-containing Otsuka Normal Saline
5% Glucose: OTSUKA GLUCOSE INJECTION 5% (from Otsuka Pharmaceutical Factory Co., Ltd.)
5% Glucose TD: 3% (w/v) trehalose- and 5% (w/v) dextran-containing OTSUKA GLUCOSE INJECTION 5%
Ringer: Ringer's Solution "OTSUKA" (from Otsuka Pharmaceutical Factory Co., Ltd.)
Ringer TD: 3% (w/v) trehalose- and 5% (w/v) dextran-containing Ringer's Solution "OTSUKA"
Veen: Veen F Infusion (from Kowa Pharmaceutical Co., Ltd.)
Veen TD: 3% (w/v) trehalose- and 5% (w/v) dextran-containing Veen F Infusion
5-1-2 Preparation of Solution for Cell Transplantation
1) The 5% (w/v) dextran-containing Lactec injection ("LRD" solution) and the 3% (w/v) trehalose- and 5% (w/v) dextran-containing Lactec injection ("LRTD" solution) were prepared according to the method described in "1-1-2 Preparation of Solution for Cell Transplantation" in Example 1.
2) The 3% (w/v) trehalose- and 5% (w/v) dextran-containing Otsuka Normal Saline ("STD" solution) was prepared by adding and dissolving trehalose (from Hayashibara Co., Ltd.) and dextran 40 (from Meito Sangyo Co., Ltd.) in Otsuka Normal Saline (from Otsuka Pharmaceutical Factory Co., Ltd.).
3) The 3% (w/v) trehalose- and 5% (w/v) dextran-containing OTSUKA GLUCOSE INJECTION 5% ("5% Glucose TD" solution) was prepared by adding and dissolving trehalose (from Hayashibara Co., Ltd.) and dextran 40 (from Meito Sangyo Co., Ltd.) in OTSUKA GLUCOSE INJECTION 5% (from Otsuka Pharmaceutical Factory Co., Ltd.).
4) The 3% (w/v) trehalose- and 5% (w/v) dextran-containing Ringer's Solution "OTSUKA" ("Ringer TD" solution) was prepared by adding and dissolving trehalose (from Hayashibara Co., Ltd.) and dextran 40 (from Meito Sangyo Co., Ltd.) in Ringer's Solution "OTSUKA" (Otsuka Pharmaceutical Factory Co., Ltd.).
5) The 3% (w/v) trehalose- and 5% (w/v) dextran-containing Veen F Infusion was prepared by adding and dissolving trehalose (from Hayashibara Co., Ltd.) and dextran 40 (from Meito Sangyo Co., Ltd.) in Veen F Infusion (from Kowa Pharmaceutical Co., Ltd.).
5-2 Result
After preparing hMSC-BM by the method described in "1-1-3 Preparation of Mammalian Cell" in Example 1, an experiment was performed according to the procedures described in "1-2 Method" in Example 1 using the 10 solutions for cell transplantation. The results are shown in FIG. 8. The use of Otsuka Normal Saline (from Otsuka Pharmaceutical Factory Co., Ltd.), Ringer's Solution "OTSUKA" (from Otsuka Pharmaceutical Factory Co., Ltd.), or Veen F Infusion (from Kowa Pharmaceutical Co., Ltd.) as the physiological aqueous solution in the solution for cell transplantation was shown to suppress cell death when hMSC-BM were preserved for 14 days and increase the rate of living cells in the solution for cell transplantation (the comparison of "S" with "STD", the comparison of "Ringer" with "Ringer TD", or the comparison of "Veen" with "Veen TD" in FIG. 8). On the other hand, the use of OTSUKA GLUCOSE INJECTION 5% (from Otsuka Pharmaceutical Factory Co., Ltd.) was not observed to suppress cell death when hMSC-BM were preserved for 14 days (comparison of "5% glucose" with "5% glucose TD" in FIG. 8). The above results show that the effect of suppressing a decrease in the rate of living cells by the combined use of trehalose and dextran is observed when at least each of saline, lactate Ringer's solution, Ringer's solution, and acetate Ringer's solution is used as the physiological aqueous solution.

Example 6

6. Confirmation 3 of that Present Solution for Cell Transplantation has Synergistic Effect of Suppressing Decrease in Cell Survival Rate (Evaluation Using Mammalian Cell Other than hMSC-BM)
It was confirmed whether the effect of suppressing a decrease in the cell survival rate by the present solution for cell transplantation was similarly observed when mammalian cells other than hMSC-BM were used.
6-1 Material
6-1-1 Solution for Cell Transplantation
S: Otsuka Normal Saline (from Otsuka Pharmaceutical Factory Co., Ltd.)
LR: Lactec injection (from Otsuka Pharmaceutical Factory Co., Ltd.)
LRT: a 3% (w/v) trehalose-containing Lactec injection
LRD: a 5% (w/v) dextran-containing Lactec injection
LRTD: a 3% (w/v) trehalose- and 5% (w/v) dextran-containing Lactec injection
6-1-2 Preparation of Solution for Cell Transplantation
The 3% (w/v) trehalose-containing Lactec injection ("LRT" solution), the 5% (w/v) dextran-containing Lactec injection ("LRD" solution), and the 3% (w/v) trehalose- and 5% (w/v) dextran-containing Lactec injection ("LRTD" solution) were prepared according to the method described in "1-1-2 Preparation of Solution for Cell Transplantation" in Example 1.
6-2 Method
[1] RPMI medium (18 mL) (from Gibco Co., Ltd.) at room temperature was added to a 50-mL conical centrifuge tube.
[2] The cap of a preservation container (vial) in which human peripheral blood T cells (hPBT) (from CELL APPLICATIONS, INC.) were freeze-preserved was loosened to release pressure, followed by closing the cap.
[3] The cells were thawed while slightly stirring in an incubator at 37° C.
[4] The thawed cells were transferred to the conical centrifuge tube to which the above RPMI medium was added.
[5] Centrifugation treatment was carried out at 400×g and 25° C. for 5 minutes, and the cells were recovered by aspirating the supernatant and suspended in 10 mL/vial of PBS (from Invitrogen Co., Ltd.).
[6] The number of the cells was measured using a cell counter, and PBS (from Invitrogen Co., Ltd.) was added to $5 \times 10^5$ cells/mL, followed by cooling with ice.
[7] The cell suspension (0.5 mL) was dispensed into each of 12 15-mL conical centrifuge tubes using FINPIPETTE (100 to 1,000 μL) and subjected to centrifugation treatment at 400×g and 25° C. for 5 minutes to recover the cells.

[8] The supernatant was aspirated/removed, and hPBT were suspended in each of the 5 solutions for cell transplantation and then preserved in a refrigerator (under conditions of 4° C.). To measure the cell survival rate before preservation, the supernatant after centrifugation treatment was aspirated/removed, and the resultant was then suspended in PBS (from Invitrogen Co., Ltd.), immediately followed by taking a portion (20 μL) of the suspension, mixing the portion with 20 μL of Trypan blue stain solution (from Gibco Co., Ltd.), and then measuring the total number of the cells and the number of dead cells using a cell counter under a microscope to evaluate the rate of living cells (see "P" in FIG. 9).

[9] After preserving hPBT in the solution for cell transplantation, stirring (5 times pipetting at a liquid volume of 250 μL) was gently performed in a state in which the end of a tip was inserted to a position visually at on the order of 5 mm from the bottom to make cells in a suspended state at day 1, day 3, day 7, and day 14 of preservation, and a portion (20 μL) of the suspension was taken into a 1.5-mL microtube, mixed with 20 μL of Trypan blue stain solution (from Gibco Co., Ltd.), and then measured for the total number of the cells and the number of dead cells using a cell counter under a microscope to evaluate the rate of living cells.

6-3 Result

The results of evaluating the rate of living cells are shown in Table 3 and FIG. 9. The cell survival rates when hPBT was preserved in the S solution and the LR solution for 1 day were decreased to 18% and 29%, respectively ("S" and "LR" at 1 day after the start of preservation in Table 3 and FIG. 9). The cell survival rates when hPBT was preserved in the LRT solution and the LRD solution for 1 day were improved to 37% and 49%, respectively, without significant difference ("LRT" and "LRD" at 1 day after the start of preservation in Table 3 and FIG. 9). On the other hand, the cell survival rate when hPBT was preserved in the LRTD solution for 1 day was as high as 82% with a significant difference compared to that when preserved in the LR solution ("LRTD" at 1 day after the start of preservation in Table 3 and FIG. 9). These results show that the combined use of trehalose and dextran can effectively suppressing a decrease in the cell survival rate of hPBT.

The effect of the combined use of trehalose and dextran became more noticeable when hPBT was preserved for 3 days, 7 days, and 14 days. Specifically, the combined use of trehalose and dextran made the cell survival rate two times or more higher than the use of trehalose or dextran alone, and the combined use of trehalose and dextran was observed to have a synergistic effect ("LRTD" at 3 days, 7 days, and 14 days after the start of preservation in Table 3 and FIG. 9). Particularly for the 7-day preservation, the percentages of hPBT surviving in the LRT solution and the LRD solution were 13% and 17%, respectively, totaling 30%, whereas the percentage of hPBT surviving in the LRTD solution was as high as 57% (1.9 times), showing the high synergistic effect of the combined use of trehalose and dextran. These results show that the effect of suppressing a decrease in the rate of living cells by the combined use of trehalose and dextran is also similarly observed when mammalian cells (hPBT) other than hMSC-BM are used.

TABLE 3

Cell Survival Rate (%) When hPBT Was Preserved

| Solution for Cell Transplantation | 1 Day | 3 Days | 7 Days | 14 Days |
|---|---|---|---|---|
| S | 18 ± 12 | 4 ± 4 | 1 ± 1 | 0 ± 0 |
| LR | 29 ± 21 | 22 ± 15 | 8 ± 5 | 4 ± 3 |
| LRT | 37 ± 17 | 22 ± 11 | 13 ± 7 | 11 ± 6 |
| LRD | 49 ± 13 | 25 ± 18 | 17 ± 7 | 16 ± 7* |
| LRTD | 82 ± 7*** | 66 ± 19*** | 57 ± 14*** | 32 ± 8*** |

For "Cell Survival Rate (%)" in the above table, the percentage of living cells based on the total number of the cells is shown as the cell survival rate (%) (mean±standard deviation, [n=6]. "*" and "***" in the table show that statistically significant differences (P<0.05 and P<0.001, respectively) against LR exist by Dunnett's test. The cell survival rate before preservation was "92±3(%)". For the 5 types of the "Solution for Cell Transplantation" in the above table, see "6-1-1 Solution for Cell Transplantation" in Example 6.

INDUSTRIAL APPLICABILITY

The present invention can provide a good-quality cell suspension capable of suppressing a decrease in the cell survival rate when the cell suspension containing stem cells, such as MSC, and leukocytes, such as T cells, is preserved for a long period of time, and thus is useful in the field of medical transplantation in regenerative medicine or the like and the field of cancer treatment.

The invention claimed is:

1. A method for preserving a mammalian cell in a physiological aqueous solution for cell transplantation, the method comprising preserving the mammalian cell for 3 to 14 days in a physiological aqueous solution for cell transplantation, said physiological aqueous solution further comprising 2.0 to 6.0% w/v of trehalose, a derivative thereof, or a salt of trehalose or the derivative, and 4.0 to 7.0% w/v of dextran, a derivative thereof, or a salt of dextran or the derivative.

2. The method according to claim 1, wherein the physiological aqueous solution is selected from the group consisting of lactate Ringer's solution, saline, Ringer's solution, and acetate Ringer's solution.

3. The method according to claim 2, wherein the mammalian cell is a mammalian mesenchymal stem cell or mammalian T cell.

4. The method according to claim 1, wherein the mammalian cell is a mammalian mesenchymal stem cell or mammalian T cell.

5. The method according to claim 4, wherein the mammalian mesenchymal stem cell is a human mesenchymal stem cell from bone marrow and the mammalian T cell is a human peripheral blood T cell.

6. A method for preserving a mammalian cell in a physiological aqueous solution for cell transplantation, the method comprising:
    adding a mammalian cell to a physiological aqueous solution for cell transplantation, said physiological aqueous solution further comprising 2.0 to 6.0% w/v of trehalose, a derivative thereof, or a salt of trehalose or the derivative, and 4.0 to 7.0% w/v of dextran, a derivative thereof, or a salt of dextran or the derivative to preserve the mammalian cell for 3 to 14 days, or adding trehalose, a derivative thereof, or a salt of trehalose or the derivative to 2.0 to 6.0% w/v and dextran, a derivative thereof, or a salt of dextran or the derivative to 4.0 to 7.0% w/v to a physiological aqueous solution containing a mammalian cell to preserve the mammalian cell for 3 to 14 days.

7. The method according to claim 6, wherein the physiological aqueous solution is selected from the group consisting of lactate Ringer's solution, saline, Ringer's solution, and acetate Ringer's solution.

8. The method according to claim 7, wherein the mammalian cell is a mammalian mesenchymal stem cell or mammalian T cell.

9. The method according to claim 6, wherein the mammalian cell is a mammalian mesenchymal stem cell or mammalian T cell.

10. The method according to claim 9, wherein the mammalian mesenchymal stem cell is a human mesenchymal stem cell from bone marrow and the mammalian T cell is a human peripheral blood T cell.

\* \* \* \* \*